(12) United States Patent
Chen et al.

(10) Patent No.: US 9,457,105 B2
(45) Date of Patent: Oct. 4, 2016

(54) NANO-SEAURCHIN CONTRAST AGENTS WITH PORE-FILLED GOLD NANORODS AND THE PREPARATION METHOD THEREOF

(71) Applicant: National Chiao Tung University, Hsinchu (TW)

(72) Inventors: San-Yuan Chen, Hsinchu (TW); Po-Jung Chen, Changhua County (TW); Dean-Mo Liu, Hsinchu County (TW); Shang-Hsiu Hu, Taoyuan County (TW)

(73) Assignee: National Chiao Tung University, Hsinchu (TW)

( * ) Notice: Subject to any disclaimer, the term of this patent is extended or adjusted under 35 U.S.C. 154(b) by 365 days.

(21) Appl. No.: 14/082,054

(22) Filed: Nov. 15, 2013

(65) Prior Publication Data

US 2014/0147388 A1  May 29, 2014

(30) Foreign Application Priority Data

Nov. 23, 2012  (TW) .............................. 101144067 A

(51) Int. Cl.
*A61K 49/22* (2006.01)
*A61K 49/18* (2006.01)

(52) U.S. Cl.
CPC ......... *A61K 49/225* (2013.01); *A61K 49/1887* (2013.01)

(58) Field of Classification Search
None
See application file for complete search history.

(56) References Cited

U.S. PATENT DOCUMENTS

2010/0255103 A1* 10/2010 Liong ................. A61K 9/5094
424/489

OTHER PUBLICATIONS

Li et al. Size tunable gold nanorods evenly distributed in the channels of mesoporous silica. 2008 ACS Nano 2: 1205-1212.*
Kim et al. Multifunctional uniform nanoparticles composed of a magnetite nanocrystal core and a mesoporous silica shell for magnetic resonance and fluorescence imaging and for drug delivery. 2008 Angew. Chem. Int. Ed. Engl. 47: 8438-8441.*
Luo et al. Mesoporous silica-coated gold nanorods with embedded indocyanine green for dual mode X-ray CT and NIR fluorescence imaging. 2011 Opt. Express 19: 17030-17039.*

* cited by examiner

*Primary Examiner* — Michael G Hartley
*Assistant Examiner* — Jennifer Lamberski
(74) *Attorney, Agent, or Firm* — Bever, Hoffman & Harms, LLP

(57) ABSTRACT

A nano-photoacoustic imaging agent is disclosed. The nano-photoacoustic imaging agent includes a porous carrier and a gold filling material embedded in the porous carrier. A method for the preparation of the nano-photoacoustic imaging agent is also provided.

12 Claims, 11 Drawing Sheets

NANO-SEAURCHIN CONTRAST AGENTS WITH PORE-FILLED GOLD NANORODS AND THE PREPARATION METHOD THEREOF

CROSS-REFERENCE TO RELATED APPLICATION AND CLAIM OF PRIORITY

This application claims the benefit of Taiwan Patent Application No. 101144067, filed on Nov. 23, 2012, at the Taiwan Intellectual Property Office, the disclosures of which are incorporated herein in their entirety by reference.

FIELD OF THE INVENTION

The present invention relates to a nano-photoacoustic imaging agent and the preparation method thereof, and more particularly to a nano-photoacoustic imaging agent for photoacoustic imaging and cancer treatment and the preparation method thereof.

BACKGROUND OF THE INVENTION

In many western countries, a photosensitizer is used to kill cancer cells in the treatment of cancer with the goal of causing minimum harm to the organs and tissues of body. These methods can avoid injury and other negative effects caused by a surgery, and they also reduce the recovery time of the patents. The theory of the photothermal therapy is based on a medium which can convert light into heat to kill the adjacent cancer cells in the process of light-heat conversion. The most familiar source of photosensitizer materials is organic molecules. In a treatment period of 1-30 days, as a result of exposure of the organic photosensitizer to illumination, too much heat generation would affect the body tissues surrounding the cancer cells. Indeed, to reduce the risk that normal organs would be damaged by the heat treatment, developing nano-materials with high efficiency of light-heat conversion would reduce the treatment time substantially. There have recently been many studies focusing on photothermal and photoacoustic imaging. The starting point is based on various types of nanogold, such as a gold nanorod, a gold nanoshell and a gold nanobox to develop a photothermal therapy, especially for photoacoustic imaging agent. However, there are still some substantial problems with the current applications.

At present, various developed photoacoustic imaging agents do not have sufficient imaging effects or retain optical characteristics for a long time. Conventional photoacoustic imaging systems only use nanogold, in which the stability for light and heat is very low under laser, and the nanogold can not actually achieve the purposes of perfect imaging and stability in the bodies of the subjects. Under the illumination of a pulsed laser, the nanogold will deform, thereby losing some of the original optical characteristics by the effect of local high temperature in a short time. Although the nanogold has effects of light and heat, the synthesized nanogold has defects of high toxicity and low biocompatibility, and thus the surface thereof has to be modified, which is time-consuming and troublesome.

In order to overcome the drawbacks in the prior art, a nano-contrast agent with seaurchin structure and the preparation method thereof are disclosed. The particular design in the present invention not only solves the problems described above, but is also easily implemented. Thus, the present invention has utility for the industry.

SUMMARY OF THE INVENTION

The present invention makes use of the combination of a mesoporous sphere and a gold rod to design and prepare a multifunctional nano-photoacoustic imaging agent, which not only has high thermal stability and the function of thermal treatment, but can also be used in photoacoustic imaging systems to synchronously monitor and diagnose. The gold rod is grown into silica mesoporous to form seaurchin structure as a nano-photoacoustic imaging agent. Under the illumination of a pulsed laser, the nano-photoacoustic imaging agent still retains the original optical characteristics and high thermal stability so as to substantially enhance the imaging stability of the nano-photoacoustic imaging agent. When the nano-photoacoustic imaging agent reach the location of the tumor by magnetic guiding, the photoacoustic imaging system is used to detect the location of the tumor cells, and the ongoing use of the external laser stimulates the nano-photoacoustic imaging agent to provide local thermal therapy and photoacoustic imaging to tumor simultaneously.

In accordance with one aspect of the present invention, a nano-photoacoustic imaging agent is disclosed. The nano-photoacoustic contrast agent includes a mesoporous carrier and a gold rod along with $Fe_3O_4$ nanoparticles embedded within the mesoporous carrier.

In accordance with another aspect of the present invention, a method for preparing a nano-nano-photoacoustic imaging agent is disclosed. The method includes steps of (a) providing a mesoporous carrier; (b) loading $Fe_3O_4$ nanoparticles in the mesoporous carrier and (c) then loading a growing seeds; and (d) causing the growing seeds to grow into a gold rod.

In accordance with a further aspect of the present invention, a nano-nano-photoacoustic imaging agent is disclosed. The nano-nano-photoacoustic imaging agent includes a porous carrier and a gold-filled material embedded in the porous carrier.

The above objects and advantages of the present invention will become more readily apparent to those ordinarily skilled in the art after reviewing the following detailed descriptions and accompanying drawings.

Figure 3:
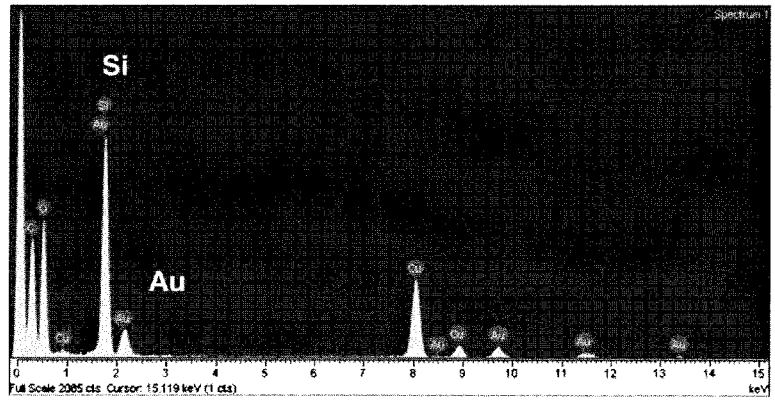
Figure 4:
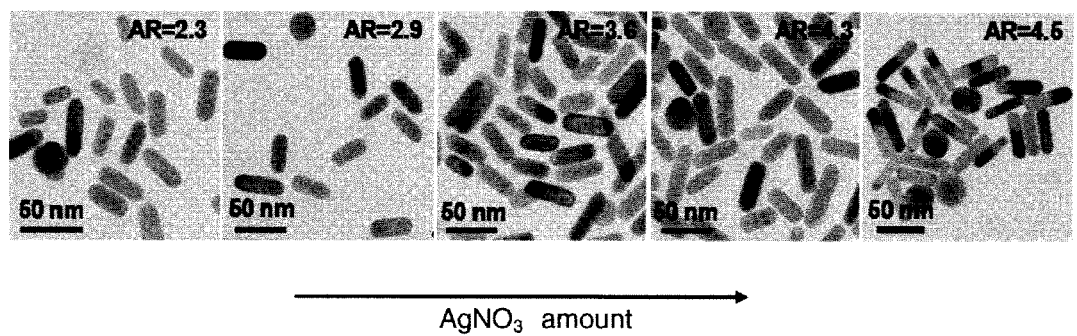
Figure 5:
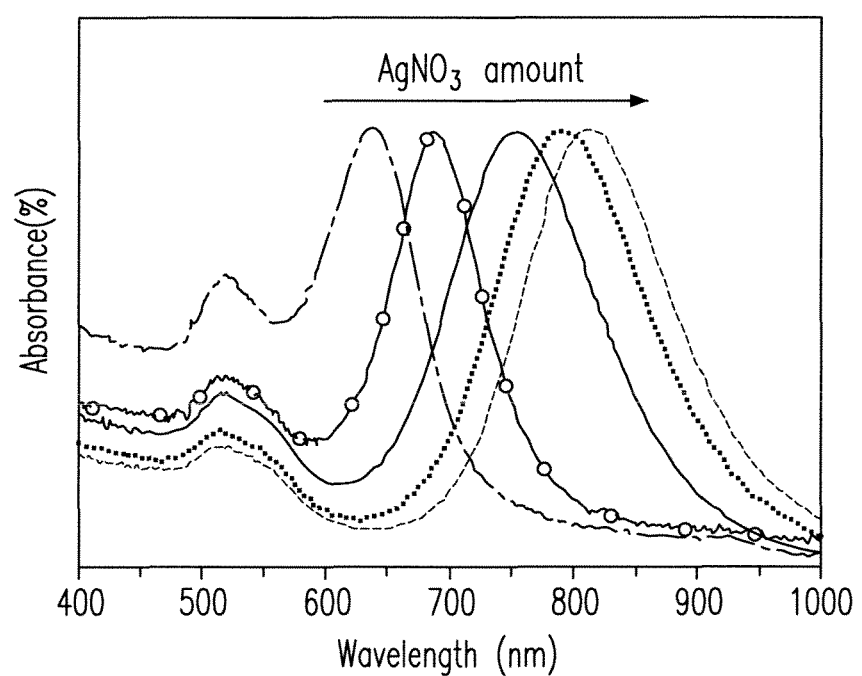
Figure 6A:
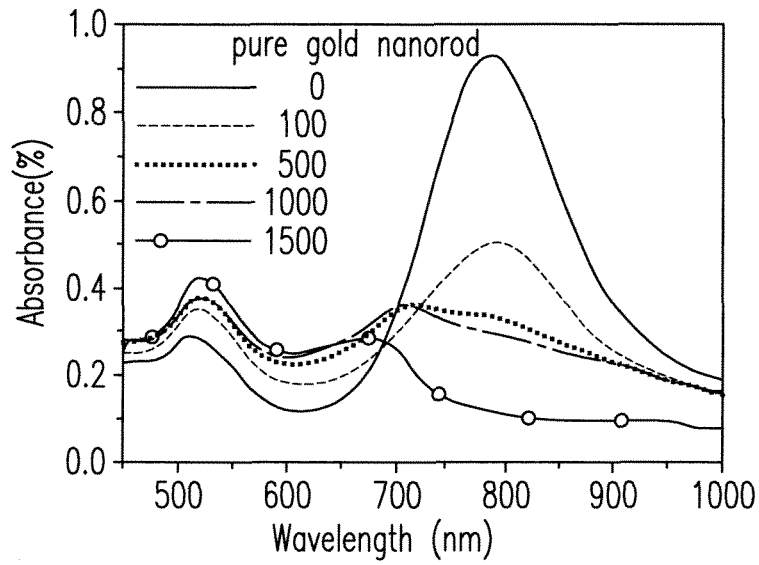
Figure 6B:
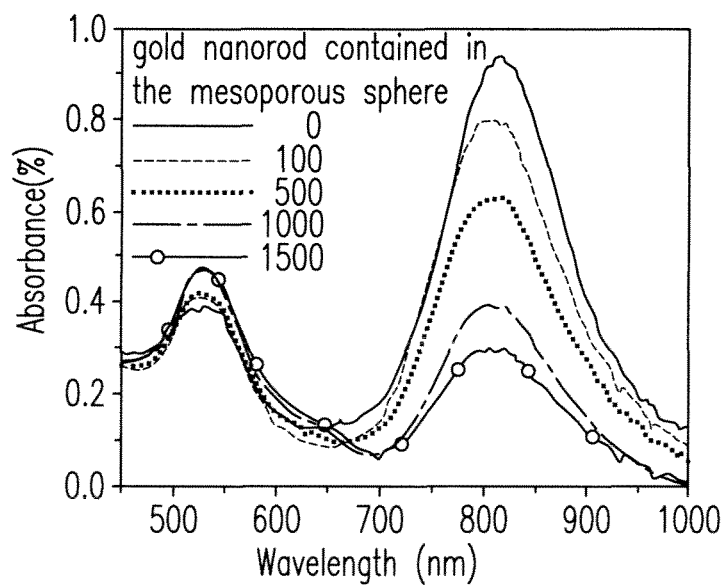
Figure 7A:
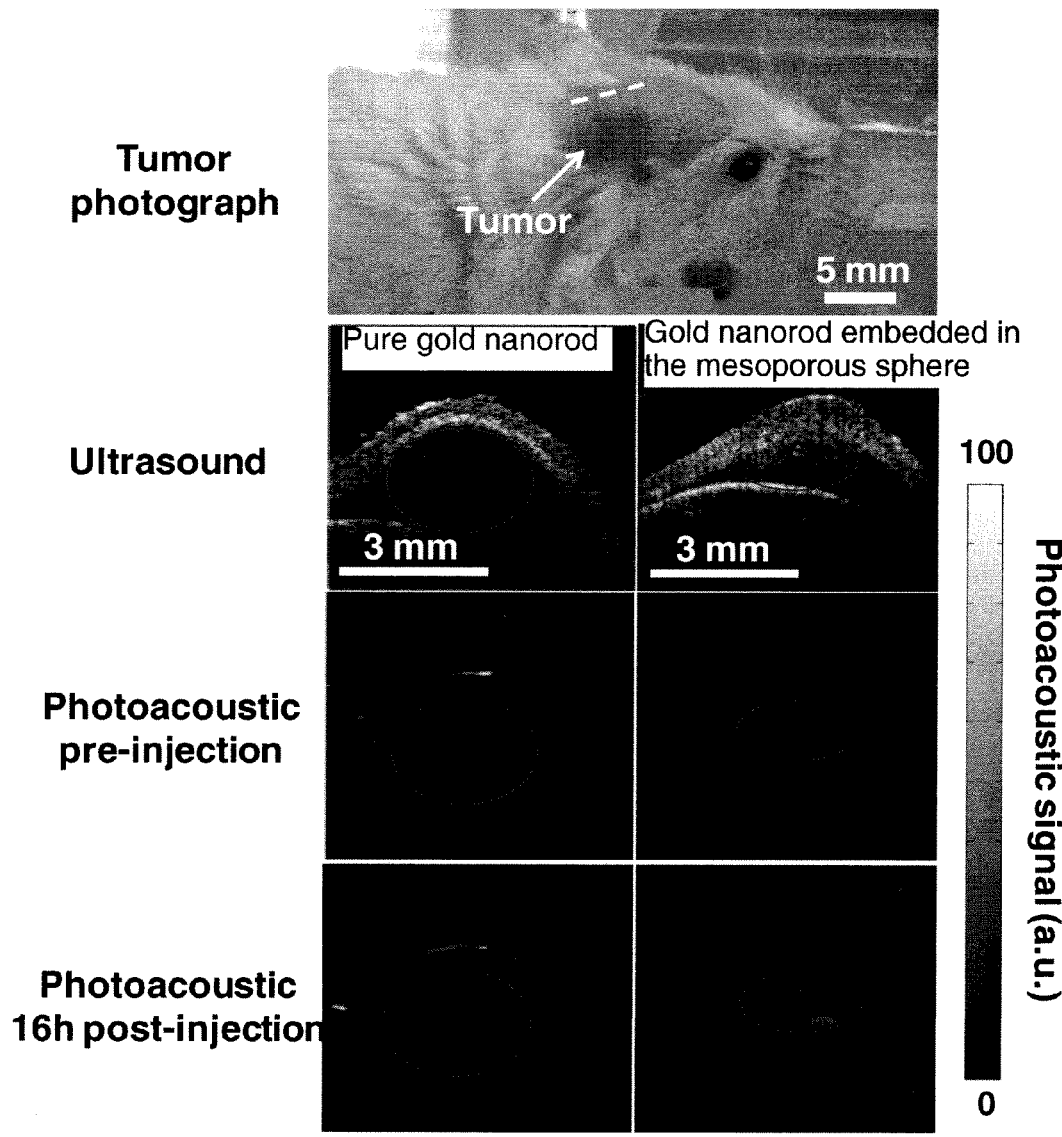
Figure 7B:
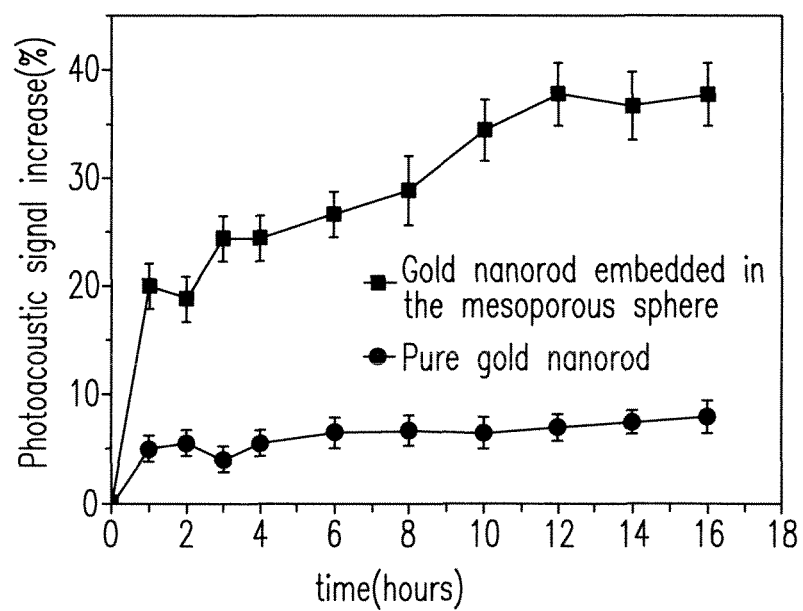
Figure 8A:
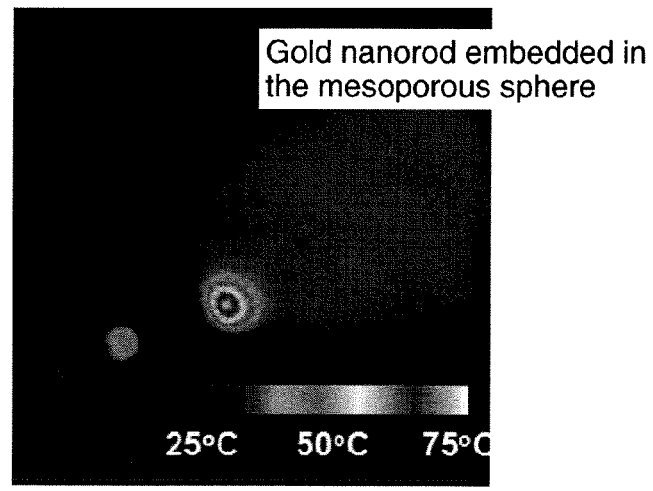
Figure 8B:
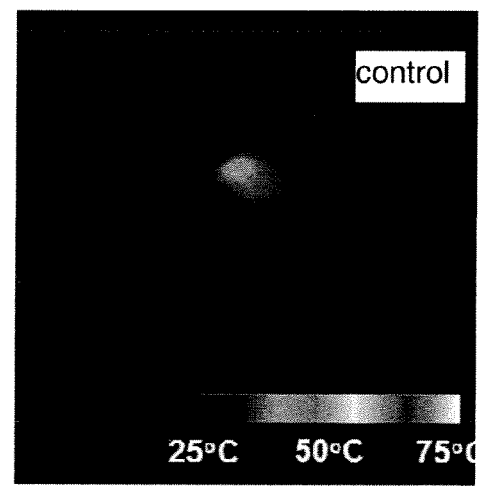
Figure 8C:
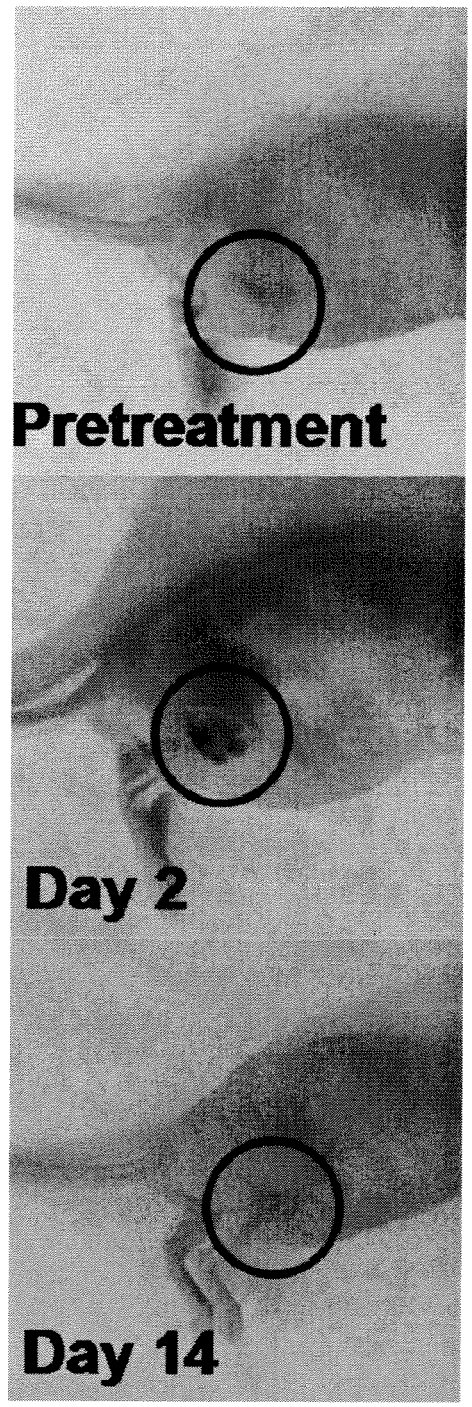
Figure 8D:
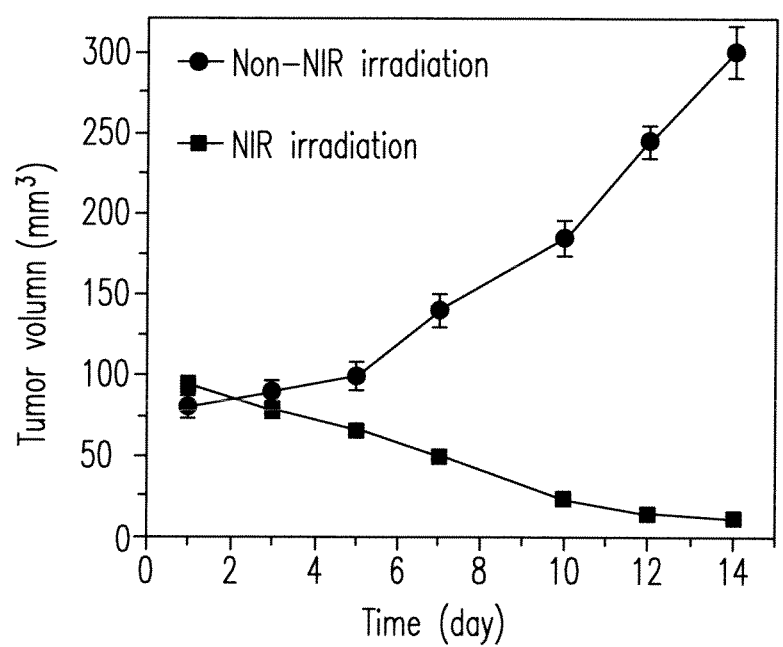
Figure 9:
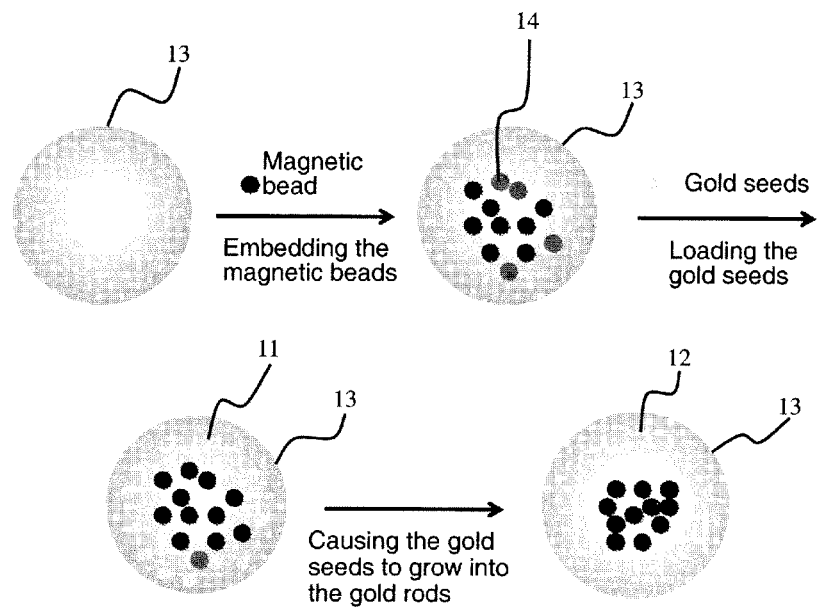
Figure 10:
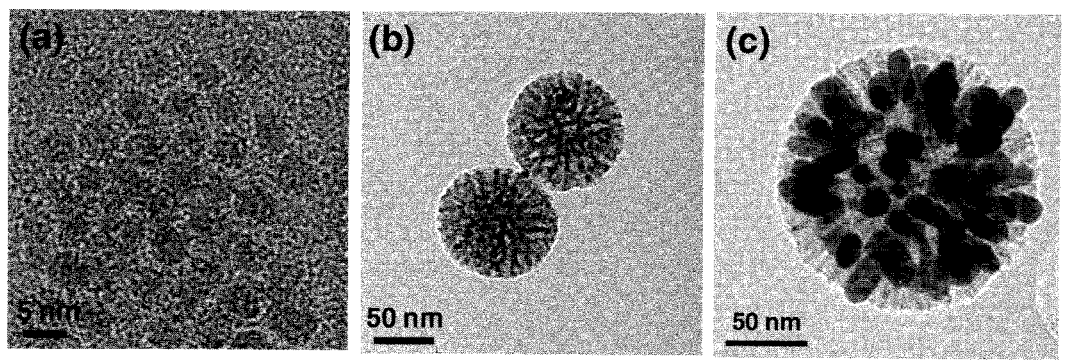
Figure 11A:
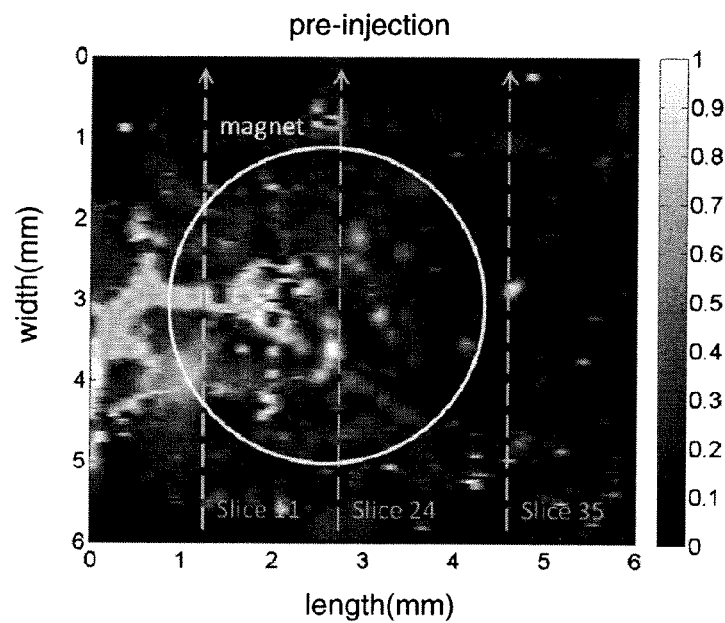
Figure 11B:
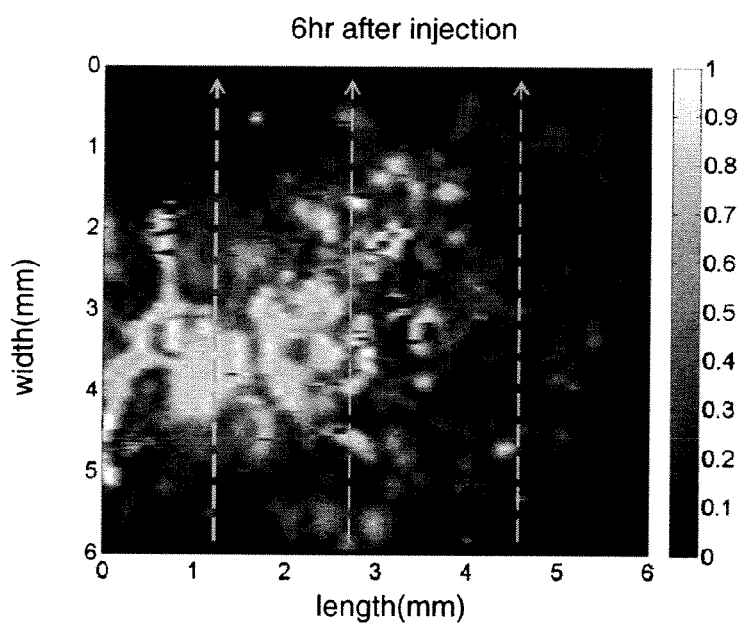

(b) shows a photograph of the mesoporous sphere as taken by the transmission electron microscope;

(c) shows the gold seeds embedded in the mesoporous sphere;

(d) shows the gold rods embedded in the mesoporous sphere;

(e) shows a high resolution photograph of the gold rods embedded in the mesoporous sphere; and (f) shows a photograph from an electron microscope where the mesoporous sphere is deformed and partial melted;

FIG. 3 shows an elemental analysis spectrum of the mesoporous sphere in which the gold rod is embedded;

FIG. 4 shows how the aspect ratio of the gold rods are modified by increasing the amount of silver nitrate;

FIG. 5 shows changes in the spectrum absorption range of the mesoporous sphere in which the gold rods are embedded as the amount of silver nitrate is increased;

FIG. 6(a) shows the change of the absorption spectrum of the pure gold rod under the illumination of a pulsed laser;

FIG. 6(b) shows the change of the absorption spectrum of the mesoporous sphere with pore-filled gold nanorods under the illumination of a pulsed laser;

FIG. 7(a) shows the photoacoustic imaging signals of the pure gold rod and the mesoporous sphere with pore-filled gold nanorods in a laboratory mouse;

FIG. 7(b) shows the signal strength analysis of the photoacoustic imaging of the pure gold rod versus the mesoporous sphere with pore-filled gold nanorods in mice;

FIG. 8(a) shows the thermal effect generated in the mouse injected with the mesoporous sphere with pore-filled gold nanorods in a vein;

FIG. 8(b) shows that there is no thermal effect in the mouse without the injection of the mesoporous sphere with pore-filled gold nanorods;

FIG. 8(c) shows the thermal therapy process resulting from the illumination of the continued laser light;

FIG. 8(d) shows the size of the tumors with and without the thermal therapy;

FIG. 9 shows the flow chart of the preparation of the magnetic nano-photoacoustic imaging agent in which the gold rod is embedded in the magnetic mesoporous sphere;

FIG. 10 shows: (a) a photograph of iron oxide nanoparticles as taken by the transmission electron microscope;

(b) a photograph of the nanobeads of iron oxide nanoparticles embedded in the mesoporous sphere, which form a magnetic mesoporous sphere; and (c) a photograph of the gold nanorods grown in the magnetic mesoporous sphere;

FIG. 11(a) shows the photoacoustic imaging of the magnetic nano-photoacoustic imaging agent before injection; and FIG. 11(b) shows the photoacoustic imaging of the magnetic nano-photoacoustic imaging agent after injection.

DETAILED DESCRIPTION OF THE PREFERRED EMBODIMENT

The present invention will now be described more specifically with reference to the following embodiments. It is to be noted that the following descriptions of the preferred embodiments of this invention are presented herein for the purposes of illustration and description only; they are not intended to be exhaustive or to be limited to the precise form disclosed.

The present invention utilizes a mesoporous material and gold rods to form a photoacoustic imaging agent where the gold nanorods are grown into a mesoporous sphere. The effect of photoacoustic imaging is achieved as the gold nanorods absorb the laser light. Because of the protection of the mesoporous material, the gold nanorods retain their original superior optical characteristics during the illumination under much higher laser pulses, and thus the purposes of stable photoacoustic signal and highly efficient hyperthermia effect can be achieved simultaneously.

Embodiment 1

Figure 1:
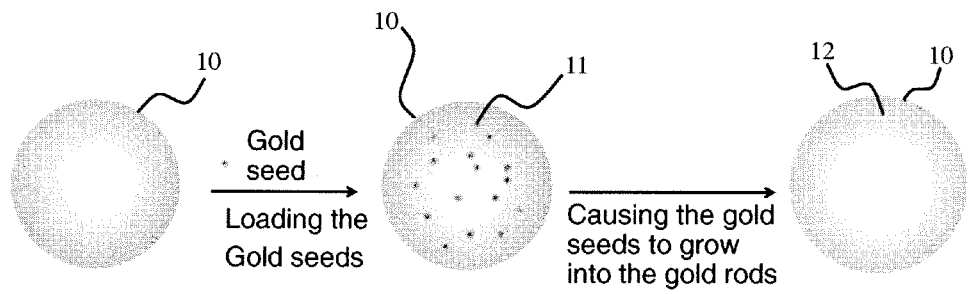
FIG. 1 shows the flow chart of preparing the nano-photoacoustic imaging agent in which a gold rod is embedded in the mesoporous sphere.
Figure 2:
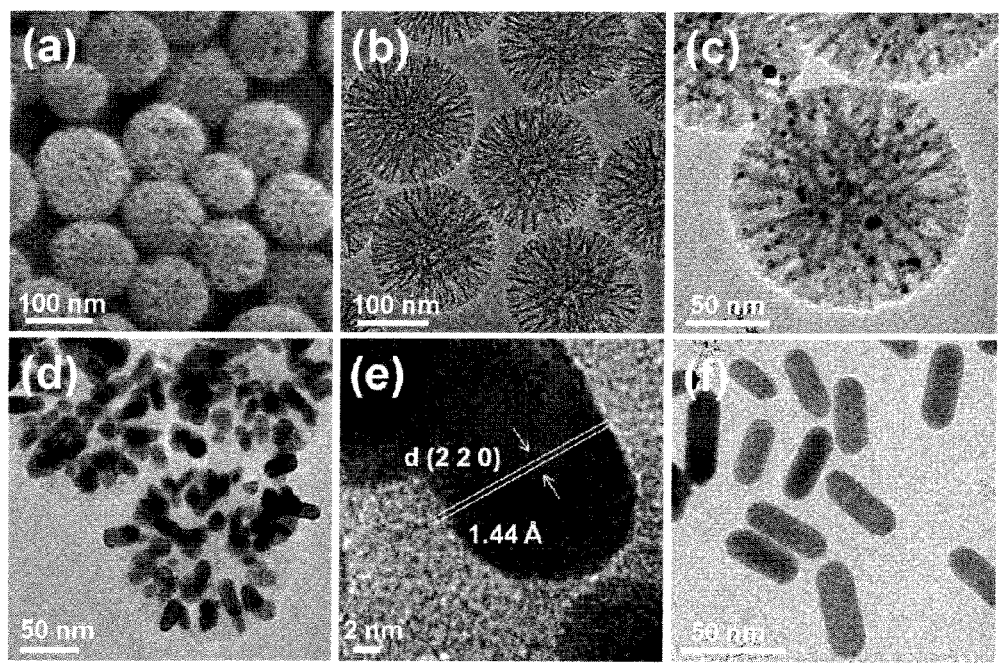
FIG. 2 shows: (a) a photograph of the mesoporous sphere as taken by the scanning electron microscope.

Please refer to FIG. 1, which shows the flow chart of the preparation of the nano-photoacoustic imaging agent in which gold nanorods are grown into the mesoporous sphere. First, a mesoporous material 10 is prepared as a carrier. The mesoporous material 10 in the present invention can be silicon dioxide. The mesoporous material 10 has a diameter ranging from 20 nm to 5000 nm, and has a plurality of pores, each of which has a diameter ranging from 5 nm to 50 nm. After the seed-carrying nanobeads (AuSNBs) 11 were immersed into the gold growth solution, the growth of gold seeds occurred as evidenced by the color change of the mixture, forming the silica mesoporous material 10 with the Au grew into a nanorod geometry 12 to fill up the nanocavity of silica mesoporous matrix 10 to form AuR-filled nanoseaurchin structures. The details of the implementation method are as follows.

Cetyltrimethylammonium bromide (CATB) is dissolved in water and the solution is heated to 70° C. to dissolve and disperse the CATB. Then, Tetraethylorthosilicate (TEOS), styrene monomer, lysine and 2,2'-azobis (2-amidinopropane) dihydrochloride (AIBA) are added to the solution and stirred for 4 hours. The resulting white precipitate is collected by centrifugation and is washed several times by a mixture of methanol and water in a ratio 1:1. Afterward, the collected precipitate is dissolved in methanol, and then hydrochloric acid is added thereto and stirred in a reaction for 24 hours. Then, the precipitate is collected to obtain the mesoporous nano-sphere of silicon dioxide. The precursor of nano-gold, hydrogen tetrachloroaurate (III) trihydrate ($HAuCl_4$), is reacted with sodium borohydride ($NaBH_4$) to form the seeds of the nano-gold, and then the above-mentioned synthesized mesoporous sphere is added thereto and stirred for 1 hour. The product, the gold seeds 11, are thus grown in the mesoporous spheres are collected by centrifugation. Finally the formulated growing solution including CTAB, hydrogen tetrachloroaurate (III) trihydrate, silver nitrate and L-ascorbic acid is added to the mesoporous spheres filled with gold seeds, and the mixture is stirred for 24 hours to obtain the nano-medium of the mesoporous spheres filled with the gold rods.

The nano-photoacoustic imaging agent characteristics of the mesoporous spheres filled with gold nanorods disclosed in the present invention are shown in the analysis from the scanning electron microscope and transmission electron microscope in FIGS. 2(a)~(f). After the above preparation method, the gold nanorods are indeed embedded in the mesoporous sphere. By employing the nano-carrier mesoporous silica, a large number of gold nanorods fill in the pores to achieve the requirement of protecting the gold nanorods to allow them to retain stable light and heat characteristics of the therapeutic agent. In addition, the process can be performed between 10° C. and 70° C., i.e. at room temperature, and thus there is no risk of a high temperature environment and the preparation is simple and fast. The nano-photoacoustic imaging agent where the gold nanorods are embedded in the mesoporous spheres is identified by energy-dispersive X-ray spectroscopy in the present invention. As shown in FIG. 3, in the elemental analysis spectrum, the absorption peaks of silicon (Si) and gold (Au) are observed clearly, which proves that the gold rods are indeed embedded in the mesoporous spheres. To make a further demonstration, the mesoporous spheres are measured by a specific surface area analysis instrument, Brunauer-Emmett-Teller (BET), to see whether there is any change in the specific surface area following the growth of the gold rods. As shown in Table 1, the surface area of the original mesoporous spheres is up to 860 m²/g. After the growth of the gold nanorods into mesoporous, both the surface of the mesoporous and the size of pores decrease substantially, which proves that the gold nanorods are indeed embedded in the mesoporous spheres.

TABLE 1

|  | surface area (m²/g) | pore volume (cc/g) | pore diameter (nm) |
|---|---|---|---|
| mesoporous sphere | 826.25 | 1.908 | 6.5 |
| gold nanorods embedded in the mesoporous sphere | 128.96 | 0.378 | 2.1 |

To regulate the spectrum absorption range of the nano-photoacoustic imaging agent, the length of the grown gold nanorods can be adjusted by controlling the amount of silver nitrate that is added in the step above. As shown in FIG. 4, as the amount of silver nitrate increases, the aspect ratio of the gold nanorods becomes larger, indicating that the length of the grown gold nanorods becomes longer. The aspect ratio of gold nanorods affects the location of the absorption peak in the spectrum. By increasing the amount of silver nitrate, the absorption spectrum shifts in the direction of red light (or longer wavelength) as shown in FIG. 5. By applying various laser lights having different wavelengths, the absorption spectrum range of the nano-photoacoustic imaging agent can be controlled.

Regarding the testing of the stability of the mesoporous spheres where gold rods are embedded for light and heat, the mesoporous spheres with the gold nanorods are compared with pure gold rods, as shown in FIGS. 6(a)~(b). After the gold nanorods were illuminated by 100 flashes of the pulsed laser, the absorbance spectrum intensity of the gold nanorods decreases by about 30%. On the other hand, the absorbance spectrum intensity of the gold nanorods embedded in the mesoporous spheres only decreased about 10%. Along with an increase of the flashes of the pulsed laser, the absorbance spectrum of the pure gold nanorods clearly moves in the direction of blue light, which indicates that the gold nanorods are being deformed or melted by the light and heat of the laser, as shown in the changes of the absorbance spectrum. By comparison, along with the increase of the flashes of the pulsed laser, the absorbance spectrum of the gold nanorods embedded in the mesoporous spheres decreases, but no blueshift occurs in the absorbance spectrum, which indicates that gold nanorod-containing mesoporous nanobeads with exceptionally efficient and stable photoacoustic imaging under the conditions of light and heat.

Regarding the property of photoacoustic imaging of the gold nanorods embedded in the mesoporous spheres, colon cancer tumor cells from the mouse were transplanted to the scalp of the mouse as shown in FIG. 7(a). The gold nanorods embedded in the mesoporous spheres were injected into the mouse via intravenous injections and the pure gold nanorods used as a control. After circulation, the changes in the photoacoustic signals were measured. Prior to the injections, both the gold nanorods embedded in the mesoporous spheres and the pure gold nanorods do not have photoacoustic signal. After 16 hours of circulation, the photoacoustic signal of the gold nanorods embedded in the mesoporous spheres clearly increased, but the pure gold rods still did not emit a signal. After data processing, the photoacoustic signal of the gold nanorods embedded in the mesoporous spheres was about 4.7 times that of the pure gold nanorods as shown in FIG. 7(b). The gold nanorods embedded in the mesoporous spheres not only raised the strength of the photoacoustic signal, but also increased the concentration of the nano-photoacoustic imaging agents near the tumor tissue, causing the nano-photoacoustic imaging agents to enter the tumor tissue to increase the photoacoustic signal.

In addition, the gold nanorods embedded in the mesoporous spheres not only have the characteristic of enhancing the strength of the photoacoustic signal, but also have the thermal therapy effect due to light-heat conversion. The gold nanorods embedded in the mesoporous spheres were injected into the tumor mouse via intravenous injection. After 4 hours of circulation, the tumor size was affected by continual laser light. FIG. 8(a) shows an immediate thermal effect in the tumor size of the mouse injected with the mesoporous spheres with pore-filled gold nanorods. By contrast, in FIG. 8(b), there is no thermal effect in the tumor size of the untreated mouse. Please refer to FIG. 8(c), which is the thermal therapy process via the illumination from the continual laser light. It can be seen that the tumor size of the mouse almost disappeared after 14 days. After calculation, FIG. 8(d) shows that the gold nanorods embedded in the mesoporous sphere indeed had excellent therapeutic effect. The application of continual laser light can release heat continuously or in stages, both of which achieve the purposes of the present invention.

The nano-photoacoustic imaging agent of the present invention has characteristics of high stability for light and heat, high biocompatibility and low toxicity, and has very good performance Regarding the therapy and imaging, which is an important breakthrough for nano-biology and medicine technologies.

Embodiment 2

Please refer to FIG. 9, which shows the flow chart for the preparation of the magnetic nano-photoacoustic imaging agent in which the gold nanorods are embedded in the magnetic mesoporous spheres. First, the magnetic beads 14 are embedded in mesoporous spheres 13 to form magnetic mesoporous spheres. Then the gold seeds 11 enter the pores of the mesoporous spheres 13 and subsequently grow into the gold nanorods 12. The magnetic beads 14 can be made of iron oxide, manganese ferrite ($MnFe_2O_4$), iron alloy such as FePt, or other beads having magnetic properties. By introducing the magnetic beads 14 into the nano-photoacoustic imaging agent, the nano-photoacoustic imaging agent has magnetic properties. Through the use of magnetic guidance, a substantial amount of the magnetic nano-photoacoustic imaging agent can be concentrated in a specific location. The magnetic nano-photoacoustic imaging agent accumulates in a high concentration, and thus the light and acoustic signal is amplified several times, which increases the therapeutic effect.

First, the synthesized mesoporous spheres in Embodiment 1 are dissolved in water, and then 5 nm magnetic ferric oxide beads are added thereto. The ferric oxide beads become embedded in the mesoporous spheres via capillarity and form the magnetic mesoporous spheres. The precursor of nano-gold, hydrogen tetrachloroaurate (III) trihydrate is first reacted with sodium borohydride to form the seeds of the nano-gold, and then the above-mentioned synthesized magnetic mesoporous spheres are added thereto and stirred for 1 hour. The product, the gold seeds 11 embedded in the magnetic mesoporous spheres are collected by centrifugation. Finally, the formulated growth solution including CTAB, hydrogen tetrachloroaurate (III) trihydrate, silver nitrate and L-ascorbic acid is added to the magnetic mesoporous spheres filled with gold seeds, and the mixture is stirred for 24 hours to obtain the nano-photoacoustic imaging agent of the magnetic mesoporous spheres with the gold nanorods embedded therein.

As the photograph from transmission electron microscope shows (FIGS. 10(a)~(c)), the ferric oxide nanobeads such as iron oxide nanoparticles are indeed embedded in the mesoporous spheres, and the gold nanorods are indeed grown in the magnetic mesoporous spheres.

Regarding the properties of photoacoustic imaging of the magnetic nano-photoacoustic imaging agent, the colon cancer tumor cells of the mouse were transplanted to the scalp of the mouse. The gold nanorods embedded in the magnetic mesoporous spheres were injected into the mouse via intravenous injection. After circulation, the changes in the photoacoustic signals were measured. Please refer to FIG. 11(a), which shows the photoacoustic imaging before the injection of the magnetic nano-photoacoustic imaging agent. A powerful magnet was placed on top of the mouse's head (the circle in the figure is the magnet). After 6 hours of circulation, the photoacoustic signal from the gold nanorods embedded in the magnetic mesoporous spheres increased significantly (FIG. 11(b)). The gold nanorods embedded in the magnetic mesoporous spheres not only increased the strength of the photoacoustic signal, because of magnetic guidance, the concentration of the magnetic nano-photoacoustic imaging agent near the tumor tissue also increased substantially, which caused the magnetic nano-photoacoustic imaging agent enter the tumor tissue, which increased the photoacoustic signal substantially.

The gold rods embedded in the magnetic mesoporous spheres have the function of photoacoustic imaging and good ferromagnetism. Through the use of magnetic guidance, a plurality of photoacoustic imaging signals were obtained from the animal, which represents an important breakthrough for nano-biology and medical technologies.

Embodiments

1. A nano-photoacoustic imaging agent includes a mesoporous carrier and gold nanorods embedded within the mesoporous carrier.

2. The nano-photoacoustic imaging agent of Embodiment 1 further includes a magnetic nanobeads embedded in the mesoporous carrier.

3. In the nano-photoacoustic imaging agent of Embodiments 1-2, the magnetic nanobeads are one selected from a group consisting of ferric oxide ($Fe_3O_4$), manganese ferrite ($MnFe_2O_4$), FePt and a combination thereof.

4. In the nano-photoacoustic imaging agent of Embodiments 1-3, the mesoporous carrier has a spherical shape.

5. In the nano-photoacoustic imaging agent of Embodiments 1-4, the mesoporous carrier has a diameter ranging from 20 nm to 5000 nm.

6. In the nano-photoacoustic imaging agent of Embodiments 1-5, the mesoporous carrier has a plurality of pores, each of which has a diameter ranging from 5 nm to 50 nm, and at least one of the plurality of pores is filled with a gold nanorod.

7. In the nano-photoacoustic imaging agent of Embodiments 1-6, the gold nanorods has a length ranging from 5 nm to 200 nm.

8. In the nano-photoacoustic imaging agent of Embodiments 1-7, the gold nanorods has a width ranging from 1 nm to 50 nm.

9. In the nano-photoacoustic imaging agent of Embodiments 1-8, the nano-photoacoustic imaging agent is applied to one selected from a group consisting of photoacoustic imaging, tumor therapy and a combination thereof.

10. A method for the preparation of a nano-photoacoustic imaging agent includes steps of (a) providing a mesoporous carrier; (b) loading growing seeds into the mesoporous carrier; and (c) causing the growing seeds to grow into gold nanorods.

11. The method of Embodiment 10 further includes a step of embedding magnetic nanobeads in the mesoporous carrier.

12. In the method of Embodiments 10-11, the magnetic nanobeads are one selected from a group consisting of ferric oxide ($Fe_3O_4$), manganese ferrite ($MnFe_2O_4$), FePt and a combination thereof.

13. In the method of Embodiments 10-12, the method is performed in a temperature ranging from 10° C. to 70° C.

14. In the method of Embodiments 10-13, the mesoporous carrier has a spherical shape.

15. In the method of Embodiments 10-14, the mesoporous carrier has a diameter ranging from 20 nm to 5000 nm.

16. In the method of Embodiments 10-15, the mesoporous carrier has a plurality of pores, each of which has a diameter ranging from 5 nm to 50 nm, and at least one of the plurality of pores is filled with a gold nanorod.

17. In the method of Embodiments 10-16, the gold nanorod has a length ranging from 5 nm to 200 nm.

18. In the method of Embodiments 10-17, the gold nanorod has a width ranging from 1 nm to 50 nm.

19. A nano-photoacoustic imaging agent includes a porous carrier and a gold material embedded in the porous carrier.

20. In the nano-photoacoustic imaging agent of Embodiment 19, the porous carrier has a diameter ranging from 20 nm to 5000 nm and a plurality of pores, each of which has a diameter ranging from 5 nm to 50 nm, and the gold material is embedded within at least one of the plurality of pores.

Based on the above, the present invention effectively solves the problems and drawbacks in the prior art, and thus it fits the demands of the medical industry and is industrially valuable.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A nano-photoacoustic imaging agent, comprising:
a mesoporous carrier having a spherical shape;
a plurality of gold nanorods embedded within the mesoporous carrier; and
a plurality of magnetic nanobeads embedded in the mesoporous carrier, wherein the mesoporous carrier has a diameter ranging from 20 nm to 5000 nm.

2. The nano-photoacoustic imaging agent as claimed in claim 1, wherein the plurality of magnetic nanobeads are one being selected from a group consisting of ferric oxide ($Fe_3O_4$), manganese ferrite ($MnFe_2O_4$), FePt and a combination thereof.

3. The nano-photoacoustic imaging agent as claimed in claim 1, wherein the mesoporous carrier has a plurality of pores, each of which has a diameter ranging from 5 nm to 50 nm, and at least one of the plurality of pores is filled with at least one of the plurality of gold nanorods.

4. The nano-photoacoustic imaging agent as claimed in claim 1, wherein each one of the plurality of gold nanorods has a length ranging from 5 nm to 200 nm.

5. The nano-photoacoustic imaging agent as claimed in claim 1, wherein each one of the plurality of gold nanorods has a width ranging from 1 nm to 50 nm.

6. The nano-photoacoustic imaging agent as claimed in claim 1, wherein the nano-photoacoustic imaging agent is applied to one being selected from a group consisting of photoacoustic imaging, tumor therapy and a combination thereof.

7. A method for the preparation of a nano-photoacoustic imaging agent, comprising steps of:
(a) providing a mesoporous carrier having a spherical shape;
(b) embedding a plurality of magnetic nanobeads in the mesoporous carrier;
(c) loading a plurality of growing seeds into the mesoporous carrier; and
(d) causing the plurality of growing seeds to grow into a plurality of gold nanorods, wherein the mesoporous carrier has a diameter ranging from 20 nm to 5000 nm.

8. The method as claimed in claim 7, wherein the plurality of magnetic nanobeads are one being selected from a group consisting of ferric oxide ($Fe_3O_4$), manganese ferrite ($MnFe_2O_4$), FePt and a combination thereof.

9. The method as claimed in claim 7, wherein the method is performed in a temperature ranging from 10° C. to 70° C.

10. The method as claimed in claim 7, wherein the mesoporous carrier has a plurality of pores, each of which has a diameter ranging from 5 nm to 50 nm, and at least one of the plurality of pores is filled with at least one of the plurality of gold nanorods.

11. The method as claimed in claim 7, wherein each one of the plurality of gold nanorods has a length ranging from 5 nm to 200 nm.

12. The method as claimed in claim 7, wherein each one of the plurality of gold nanorods has a width ranging from 1 nm to 50 nm.

* * * * *